United States Patent [19]

Gentelia et al.

[11] Patent Number: 5,254,083
[45] Date of Patent: Oct. 19, 1993

[54] SUCTION AND IRRIGATION APPARATUS

[75] Inventors: John S. Gentelia, Madison; Frank Williams, Utica; Alfred Solan, Cassville; Sharyn Longo, Frankfort, all of N.Y.

[73] Assignee: Conmed Corporation, Utica, N.Y.

[21] Appl. No.: 833,000

[22] Filed: Feb. 10, 1992

[51] Int. Cl.⁵ .............................................. A61M 1/00
[52] U.S. Cl. ...................................... 604/35; 604/34; 604/250; 604/902; 251/7
[58] Field of Search .................. 604/30, 34, 35, 119, 604/246, 250, 902; 137/595; 251/4, 6–10; 433/95, 100

[56] References Cited

U.S. PATENT DOCUMENTS

| | | | |
|---|---|---|---|
| 1,677,453 | 7/1928 | Jones | 137/595 |
| 4,061,142 | 12/1977 | Tuttle | |
| 4,524,802 | 6/1985 | Lawrence et al. | |
| 4,531,912 | 7/1985 | Schuss et al. | 433/80 |
| 4,536,180 | 8/1985 | Johnson | 604/268 |
| 4,634,092 | 1/1987 | Daniell et al. | |
| 4,688,753 | 8/1987 | Tseng et al. | |
| 4,696,669 | 9/1987 | Menhusen | |
| 4,702,733 | 10/1987 | Wright et al. | |
| 4,834,702 | 5/1989 | Rocco | |
| 4,872,837 | 10/1989 | Issalene et al. | 433/29 |
| 4,878,894 | 11/1989 | Sutter, Jr. et al. | |
| 5,035,399 | 7/1991 | Rantanen-Lee | |
| 5,120,305 | 6/1992 | Boehringer et al. | 604/35 |
| 5,188,591 | 2/1993 | Dorsey, III | 604/33 |

FOREIGN PATENT DOCUMENTS 2509485 9/1976 Fed. Rep. of Germany ...... 604/250
2117245 10/1983 United Kingdom ................ 604/902

Primary Examiner—C. Fred Rosenbaum
Assistant Examiner—Corrine Maglione
Attorney, Agent, or Firm—Larson & Taylor

[57] ABSTRACT

A suction and irrigation apparatus is provided for selectively delivering suction or irrigation fluid to a patient during surgery or the like. A pair of resilient tubes are provided which is connected with a suction source and irrigation source at one end and is connected through a Y-shaped connector at the other end with a handpiece having clamping valves thereon disposed between the ends of the resilient tubes. The handpiece has a housing with openings in the ends thereof to provide passageways for the resilient tubes. Clamping valves are mounted in the housing which are spring urged to close the resilient tubes. A bracket is slidably mounted on the sides of the handpiece housing and the bracket is slidable to a position overlying the clamping valves so as to maintain the clamping valves in an open position. When the clamping valves are held in an opened position by the bracket, the handpiece can be moved along the length of the resilient tubes to position the handpiece at any desired location. When the handpiece is located in the desired position, the bracket is removed from the handpiece to release the clamping valves to close the resilient tubes.

9 Claims, 2 Drawing Sheets

SUCTION AND IRRIGATION APPARATUS

FIELD OF THE INVENTION

The present invention relates generally to surgical medical equipment and more specifically to an apparatus for selectively delivering suction or irrigation to a surgical site.

BACKGROUND OF THE INVENTION

There are a number of devices shown in prior art references which perform the function of delivering suction or irrigation through resilient tubes together with valves for opening or closing each of the tubes in accordance with the instructions of the operating surgeon. However, such prior art devices do not fully meet the requirements of equipment which must function properly in cramped areas.

The Menhusen U.S. Pat. No. 4,696,669 discloses a hand held combination flush and suction apparatus which includes a hand held control and dispenser apparatus together with a pump assembly. There is provided a foot pedal for operating the pump and the hand held control and dispenser unit does not provide for instantaneous response nor permit the control unit to be moved to any desired position along the length of the tubes.

The Wright et al U.S. Pat. No. 4,702,733 discloses an irrigation and aspiration system which utilizes a foot pedal for selectively controlling the flow of irrigation and aspiration fluid. The system disclosed in this prior art device is expensive and does not meet the needs of a surgeon operating in a crowded environment.

There are a number of prior art references which disclose various types of clamp valves for opening and closing resilient tubes. Examples of such devices are Daniell et al U.S. Pat. No. 4,634,092; Rocco U.S. Pat. No. 4,834,702; Tseng et al U.S. Pat. No. 4,688,753; Lawrence et al U.S. Pat. No. 4,524,802; Tuttle U.S. Pat. No. 4,061,142; Sutter et al U.S. Pat. No. 4,878,894 and Rantanen-Lee U.S. Pat. No. 5,035,399. While these references disclose various types of valves for clamping and releasing resilient tubing in medical equipment, the systems disclosed do not provide all of the functions required by a surgeon to control both aspiration and irrigation.

SUMMARY OF THE INVENTION

The present invention provides a simple handpiece which readily controls irrigation and suction and which can be readily located at any desired point along the length of the resilient tubes extending between wall suction and irrigation at one end to the surgical site at the opposite end of the resilient tubes. This is achieved by providing a housing having a pair of passageways therethrough for the suction tube and the irrigation tube. A clamping valve is provided for each tube and both clamping valves are urged into a tube closed position by spring means. A slidable bracket is provided which may be positioned over the clamping valves to simultaneously maintain both of the clamping valves in an opened position. When the clamping valves are held in the opened position, the handpiece can be moved along the length of the resilient tubes to any desired position. When the hand held control is in the desired location, the bracket may be slid off the handpiece so as to release the clamping valves to a closed position. The handpiece is then in condition to be utilized by the operator in accordance with the instructions of the surgeon.

An object of the present invention is to provide an irrigation and suction handpiece in which the clamping valves may be retained in an opened position to permit the handpiece to be moved along the length of the resilient tubes.

Another object of the present invention is to provide a locking bracket for a suction and irrigation handpiece so as to retain the clamping valves in an opened position.

Other objects and many of the attendant advantages of the present invention will become apparent upon consideration of the following detailed specification in connection with the accompanying drawings wherein:

DESCRIPTION OF THE PREFERRED EMBODIMENT

Figure 1:
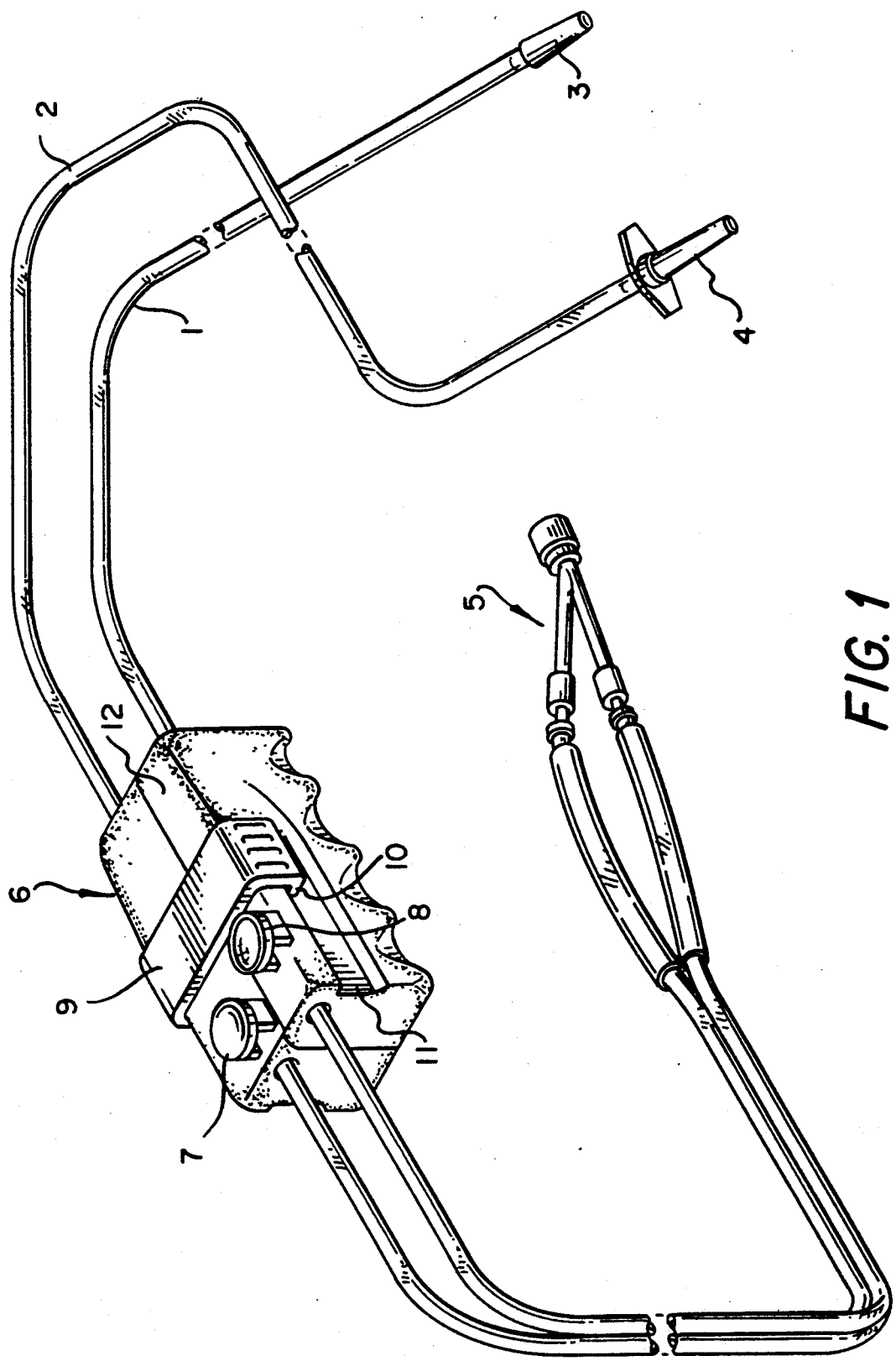
FIG. 1 is a perspective view of the irrigation and suction handpiece with the locking bracket in a position to retain the clamping valves in a closed position.

Referring now more specifically to the drawings wherein like numerals indicate like parts throughout the several views, there is shown in FIG. 1 a suction tube 1 and irrigation tube 2 which are formed of resilient plastic and which may be readily pinched to close off the passageway. At one end of tubes 1 and 2, there are provided connectors 3 and 4 respectively for attachment to suction and irrigation sources. The opposite ends of the tubes 1 and 2 are connected to a Y-shaped connector 5 which provides a single nozzle for suction or irrigation at the surgical site as required by the surgeon.

A handpiece 6 is provided with passageways therein to receive the tubes 1 and 2 and clamping valves 7 and 8 which are angularly offset with respect to each other are mounted on handpiece 6 to control the flow through suction tube 1 and irrigation tube 2, respectively. The end portion of the handpiece distal from the valves 7 and 8 is tapered and the bottom portion of the handpiece 6 is provided with recessed finger gripping areas.

There is provided a locking bracket 9 which is slidably mounted on handpiece 6. The locking bracket is provided with inturned end flanges 10 which are slidable within a recessed portion 11 on the side walls of the handpiece. As seen in FIG. 1, the end portion 12 of handpiece 6 is tapered so that when the bracket slides over the end portion 12, the bracket may be removed from the handpiece. When the bracket 9 is disposed within the recessed portion 11, it may be slid forwardly and with the clamping valves 7 and 8 depressed, the bracket serves to lock the clamping valves against the upper face of the handpiece.

Figure 2:
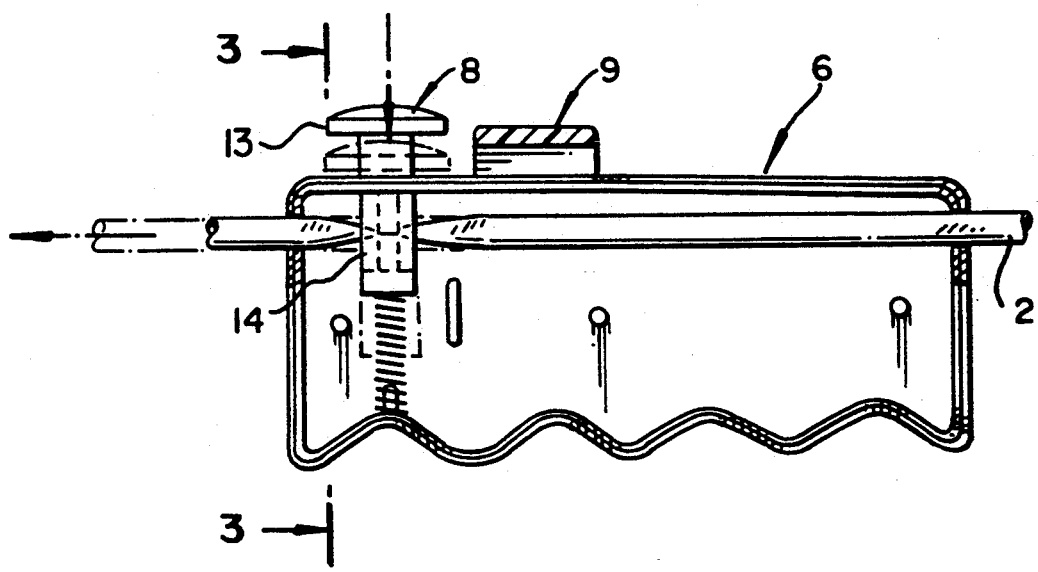
FIG. 2 is a sectional side elevational view of the handpiece showing one of the valves in closed position with a dotted line showing of the valve in open position.
Figure 3:
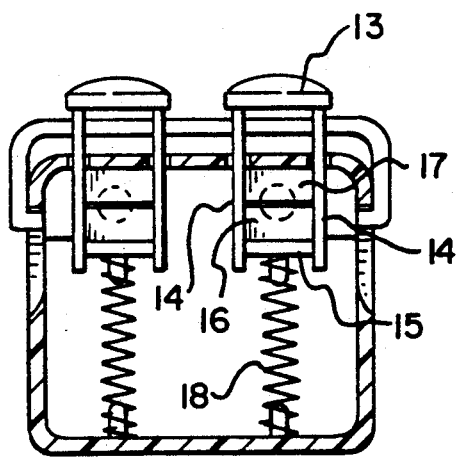
FIG. 3 is a sectional view along the line 3—3 of FIG. 2 showing both valves in closed position.
Figure 4:
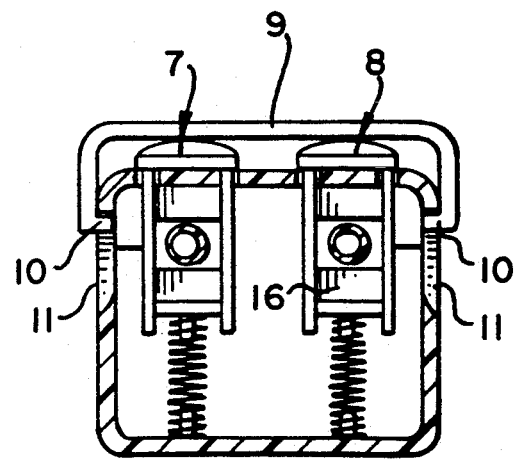
FIG. 4 is a sectional view similar to FIG. 3 showing both valves retained in an open position by means of the locking bracket.

In FIG. 2 there is shown a cross sectional view of the handpiece 6. The clamping valve 8 is shown in clamping engagement with irrigation tube 2. In this position the flow of fluid through the tube is cut off. It can be seen that the clamping valve 8 comprises an operating button 13 having a pair of integrally formed downwardly extending arms 14. These arms 14 extend through a pair of apertures formed in the top face of the handpiece. At the lower ends of the arms 14, FIG. 3 there are provided a plate 15 which is fixed to the lower end of arms 14. The upper face of plate 15 has mounted thereon a clamping bar 16 and a clamping bar 17 is mounted on the lower face of the underside of the top of handpiece 6. A compression spring 18 extends between the lower face of the plate 15 and the bottom wall of the handpiece so as to force the clamping valve 8 to its uppermost position, in which position it closes off the irrigation tube 2 between clamping bars 16 and 17 as shown in FIG. 3. When the operating button 13 on valve 8 is depressed, the clamping bar 16 releases engagement with the irrigation tube 2 so as to permit fluid flow through the tube. As shown in FIG. 4 the bracket 9 is positioned over the clamping valves 7 and 8 so as to open both the suction tube 1 and irrigation tube 2.

In use, the handpiece is adjusted at a desired location along the length of the suction tube 1 and irrigation tube 2 by sliding the locking bracket 9 over the clamping valves 2 and 8 to depress the operating buttons so as to release engagement of the clamping valves with the tubes and thus permit the tubes 1 and 2 to be slid along the length of the handpiece with the end flanges 10 of the bracket 9 extending within the recessed portion 11 of the side walls of the handpiece. With the operating buttons on clamping valves 7 and 8 depressed, the locking bracket 9 may be readily positioned directly over the valves to maintain the valves in an open position. In this position, the handpiece 6 may be positioned at any point along the length of the tubes 1 and 2 so as to enable the operator of the handpiece to be located at a position selected by the surgeon. When the handpiece is positioned at the desired location, the bracket 9 may be slid towards the end portion 12 of the handpiece so that the bracket may be removed and discarded. When the bracket is removed, the clamping valves 7 and 8 are forced upwardly by springs 18 to close the suction tube 1 and irrigation tube 2. The connector 3 at the end of suction tube 1 may then be connected with wall suction and the connector 4 on the end of irrigation tube 2 may be connected with a source of irrigation. Many modifications and variations of the present invention are possible in light of the above teachings.

What is claimed as new and is desired to be secured by Letters Patent is:

1. A suction and irrigation handpiece for controlling flow through resilient tubing comprising, top and bottom walls interconnected with a pair of sidewalls and a pair of end walls to form a hollow housing, a pair of apertures in each end wall, a pair of resilient tubes extending through said apertures to provide passageways through the housing, a pair of clamping valves extending through the top walls of the housing and engaging said resilient tubes, said clamping valves being slidable within the housing to open and close said resilient tubes, spring means within said housing and engaging said clamping valves for urging said clamping valves to a position to close the resilient tubes and releasable means on the housing and further including recesses in the sidewalls of said housing, said releasable means comprising a slidable bracket which slides in said recesses to retain said clamping valves in a position to open the resilient tubes so that the suction and irrigation handpiece can slide along the length of the resilient tubing to be positioned at any point convenient for use by the physician.

2. A suction and irrigation handpiece according to claim 1 wherein each clamping valve comprises a push button, a pair of spaced arms integral with said push button and extending perpendicularly with respect to the plane of the push button, and a pair of slots in the top wall of the housing to receive said arms.

3. A suction and irrigation handpiece according to claim 2 and further including a plate extending between the ends of the arms of the valve, remote from the push button said plate engaging said spring means to urge the plate and arms upwardly to close the resilient tube.

4. A suction and irrigation handpiece according to claim 3 and further including a pair of jaws for engaging the resilient tube, one of said pairs of jaws being secured to said plate and the other of said jaws being secured to the top of the housing whereby when the clamping valve is in the closed position, the resilient tube is closed between the pair of jaws.

5. A suction and irrigation handpiece according to claim 1 and further including handgrip recesses in the bottom wall of the housing for grasping the handpiece.

6. A suction and irrigation handpiece according to claim 1 wherein the clamping valves are offset angularly with respect to each other.

7. A suction and irrigation apparatus comprising a pair of resilient tubes having connector plugs on one end thereof for connection to a suction source and an irrigation source, the other end of said tubes being secured to a Y-shaped connector plug for selectively delivering suction or irrigation to the outlet of the Y-shaped connector plug, a handpiece including a housing having passageways therethrough for said resilient tubes and clamping valves mounted within said housing and engaging said tubes, spring means disposed within the housing and urging said clamping valves to a closed position and a slidable bracket mounted on said housing for simultaneously locking said clamping valves in an open position so that said handpiece can be readily moved to any desired position along the length of the resilient tubes.

8. A suction and irrigation apparatus according to claim 7 wherein said slidable bracket has inturned end portions and further including recesses in the side walls of said housing for engaging the inturned end portions of the bracket.

9. A suction and irrigation apparatus according to claim 7 wherein each clamping valve comprises a push button, a pair of spaced arms integral with said push button and extending perpendicularly with respect to the plane of the push button, and a pair of slots in a wall of the housing to receive said arms.

* * * * *